United States Patent [19]

Bokiau

[11] Patent Number: 4,807,391

[45] Date of Patent: Feb. 28, 1989

[54] APPARATUS FOR DISPENSING INSECTICIDE

[76] Inventor: Philippe Bokiau, Villa le Ressac. Parc de la Cote Bleue, 13620 Carry Le Rouet, France

[21] Appl. No.: 824,850

[22] Filed: Jan. 31, 1986

[30] Foreign Application Priority Data

Jun. 25, 1985 [FR] France .................... 85 09766

[51] Int. Cl.$^4$ ............................................. A01M 1/14
[52] U.S. Cl. ...................................................... 43/131
[58] Field of Search ................. 43/107, 108, 119, 120, 43/121, 122, 131, 114; 206/602, 627; 424/1

[56] References Cited

U.S. PATENT DOCUMENTS

| | | | |
|---|---|---|---|
| 890,636 | 6/1908 | Fride | 43/131 |
| 944,419 | 12/1909 | Ellis | 43/124 |
| 1,071,578 | 8/1913 | Rese | 43/114 |
| 1,795,238 | 3/1931 | Spence | 426/1 |
| 1,820,186 | 8/1931 | Gaskins | 43/131 |
| 2,004,841 | 6/1935 | Vinson | 43/131 |
| 2,328,590 | 9/1943 | Weil | 43/131 |
| 2,582,655 | 1/1952 | Schenk | 206/602 |
| 3,032,915 | 5/1962 | Giroud-Abel | 43/131° |
| 3,173,223 | 3/1965 | Dunn et al. | 43/131 |
| 3,362,616 | 1/1968 | Van Dyck | 206/602 |
| 3,550,308 | 12/1970 | Ibach | 43/131 |
| 3,864,867 | 2/1975 | Dry | 43/131 |
| 4,160,335 | 7/1979 | Von Kohorn et al. | 43/131 |
| 4,179,840 | 12/1979 | Sandefur | 43/131 |
| 4,281,471 | 8/1981 | Jenkins et al. | 43/131 |

FOREIGN PATENT DOCUMENTS 2741863 3/1979 Fed. Rep. of Germany .
2241252 3/1975 France .
0501342 3/1939 United Kingdom .

*Primary Examiner*—M. Jordan
*Attorney, Agent, or Firm*—Sandler & Greenblum

[57] ABSTRACT

A container for housing an insecticide and the insecticide itself, composed of boric acid, molasses, and flour in the proportions of 3:2:2 by weight. Such an insecticide adheres to the walls of the container and is substantially hygrometrically stable. The container includes a bottom wall and two side walls, ans is open at the top so that the volume defined by the container is substantially parallelepipedic and the container has a U-shaped transverse cross-section. In addition, the container has a self-adhering surface on the external surface of the bottom wall so that the container can be attached to any surface used by insects such as the ceiling, a vertical wall, or the ground.

8 Claims, 1 Drawing Sheet

U.S. Patent  Feb. 28, 1989  4,807,391
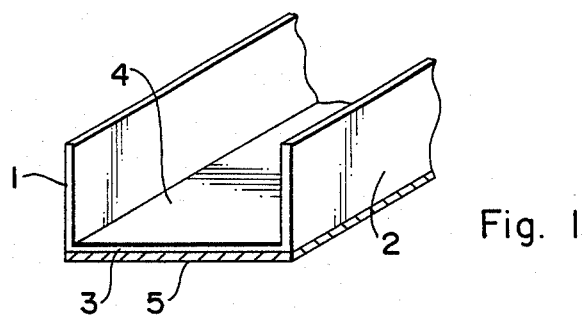
Fig. 1
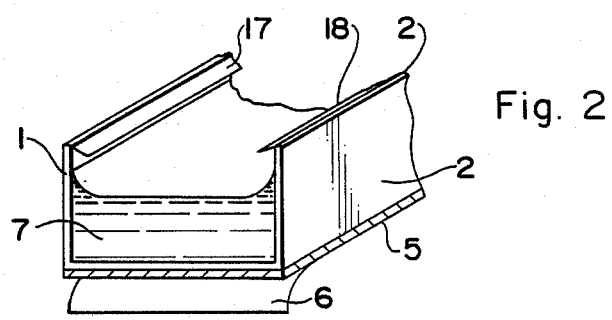
Fig. 2
Fig. 3
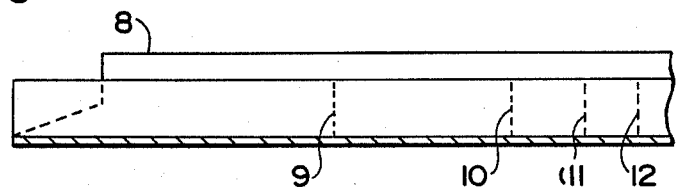
Fig. 4
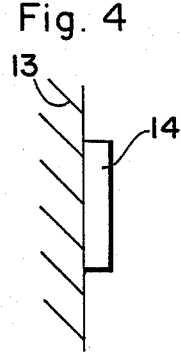
Fig. 5
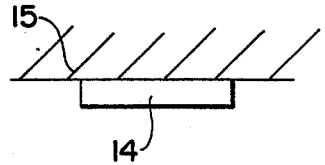
Fig. 6
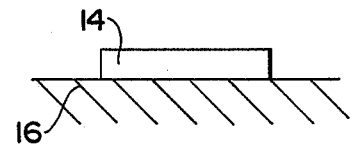

APPARATUS FOR DISPENSING INSECTICIDE

BACKGROUND OF THE INVENTION

1. Field of the Invention

The invention relates to an insecticide and an apparatus for dispensing this insecticide.

More particularly, the invention relates to an insecticide for destroying insects such as cockroaches within the home, and an apparatus for storing and transporting an insecticide, for determining the dimensions of the insecticide applied, and for attaching the apparatus at its location of use. The insecticide can be used directly after being placed in the storing apparatus.

2. Description of Pertinent Information

Numerous insecticides exist which use boric acid as a base. However, these insecticides suffer serious disadvantages when applied without dispersion on surfaces frequented by insects.

Thus, there is a need for a boric acid based insecticide that does not suffer the disadvantages of prior boric acid based insecticides.

SUMMARY OF THE INVENTION

It is an object of the present invention to overcome the disadvantages of the prior art.

The invention which achieves this objective relates to a container for housing an insecticide in combination with the insecticide itself. The container comprises two side walls and a bottom wall connecting the two side walls. The container is open at the top and the two side walls and the bottom wall form a continuous canal having a substantially U-shaped transverse cross-section and forming a substantially parallelepipedal volume therein. The bottom wall comprises an exterior surface comprising a self-adhesive lining. The insecticide comprises a substantially pasty mixture positioned in the container. The insecticide adheres to the walls of the container and the insecticide is substantially hygrometrically stable.

The insecticide comprises a boric acid base, sugar molasses, and starch comprising flour. The flour is a hygrometrical stabilizing agent. The proportion of boric acid, sugar molasses, and flour by weight is 3:2:1, respectively. In addition, the insecticide comprises an agent limiting the fluidity of the insecticide.

The container has a predetermined length and further comprises at least one perforation line extending along the side walls substantially perpendicular to the bottom wall. The at least one perforation line comprises means for separating the container along the perforation line into two containers each having a length shorter than the predetermined length of the container. In another embodiment the container comprises a plurality of spaced apart perforation lines. In still another embodiment the side walls each comprise an upper portion, and the container further comprises two retention sections positioned at the upper portions of the side walls. Each of the retention sections extends inwardly and downwardly from the upper portion of each side wall.

The self-adhesive lining comprises means for positioning the container on a vertical wall, a ceiling, or the ground. In addition, a protective film removably attached to the self-adhesive lining can also be provided.

In still another embodiment the invention relates to an insecticide for use in a container. The insecticide comprises a pasty substance adapted to adhere to the walls of the container and which is substantially hygrometrically stable. The insecticide is composed of boric acid, molasses, and a starch, and the the proportion of the boric acid, molasses, and starch is 3:2:1 by weight. The starch used can be flour.

BRIEF DESCRIPTION OF THE DRAWINGS

The invention will be better understood upon reviewing the detailed description which follows in conjunction with the attached drawings in which:

FIG. 1 illustrates an elevational perspective view of the conditioning container of the present invention;

FIG. 2 illustrates a perspective view of the conditioning container of the present invention in which the insecticide of the present invention is disposed;

FIG. 3 illustrates a side view of the conditioning container of the present invention which show perforation lines about which the container can be broken up into a plurality of separate containers; and FIGS. 4-6 illustrate schematic side views of the conditioning container of the present invention positioned on various surfaces.

DETAILED DESCRIPTION OF PREFERRED EMBODIMENTS

The present invention provides an insecticide having a viscosity which allows the insecticide to be distributed in a container without the insecticide flowing out of or within the container so that the insecticide has a stable position regardless of the positioning of the container.

The present invention relates to such an insecticide and a container for holding this insecticide. The container comprises a parallelepipedal housing whose upper surface is open and whose lower external wall is self-adhesive. The insecticide that is placed in this container has an adherent, plastic texture.

As illustrated in FIGS. 1 and 2, the present invention relates to a conditioning container or support 8 adapted to store an insecticide 7 therein. Container 8, as illustrated in FIGS. 1 and 2, comprises a container 1 meter high having a substantially U-shaped transverse cross-section and which forms a substantially parallelepipedal volume therein. Container 8 comprises two spaced apart side walls 1 and 2 which extend substantially vertically when container 8 is positioned upright as in FIG. 1, and a substantially rectilinear bottom wall 3 connecting walls 1 and 2. The top portion of container 8 is open so as to form an opening 4. The length of container 8 corresponds to the length of the surface on which the container is to be applied.

The external surface of bottom wall 3 is covered with a self-sticking or self-adhesive lining 5 having a removable protective film 6 thereon. When film 6 is removed from lining 5 so as to expose self-adhesive lining 5, self-adhesive lining 5 can be applied to a surface such as a vertical wall as seen in FIG. 4, the ceiling as seen in FIG. 5, or the ground as seen in FIG. 6, thereby attaching container 8 to these surfaces. Vertical walls 1 and 2 and bottom wall 3 form a canal therein which is adapted to receive insecticide 7 therein. Insects crawling on the surfaces to which container 8 is attached will crawl into open space 4 and the canal in container 8, thereby coming into contact with insecticide 7 which kills the insects. Insecticide 7 is in the form of a liquid, but is sufficiently adhesive and plastic so as to adhere to vertical walls 1 and 2 and bottom wall 3 without becoming removed therefrom. Substances such as boric acid in combination with concentrated sugared milk or other similar substances cannot be used for this purpose because these substances either become removed from the vertical and bottom walls of container 8, or they dry out.

The present invention overcomes these difficulties by using a boric acid and molasses base in the form of a paste, in combination with starches in the form of flour to control moisture absorption. The starches extend the effectiveness of the insecticide during extending periods of time while substantially slowing the drying out of the insecticide. The molasses base acts as bait for the insects.

The proportion of boric acid to molasses to flour in insecticide 7 by mass or weight can be 3:2:1, or in other words, one half of insecticide 7 by mass or weight is boric acid, one third of insecticide 7 by mass or weight is molasses, and one sixth of insecticide 7 by mass or weight is starch in the form of flour. In one example, when insecticide 7 has a total mass of one kilogram, the composition of insecticide 7 is: one-half kilogram of boric acid, one-third kilogram of molasses, and one sixth kilogram of starch in the form of flour. Alternatively, the preferred proportion of boric acid to molasses to starch can be 3:2:2. However, any proportion of these ingredients can be used.

The compositions of insecticide 7 noted above adheres perfectly to the inside of container 8. Further, the humectant properties of insecticide 7 are controlled in such a manner that insecticide 7 cannot become detached from the inside of container 8.

Container 8 can have a length of up to several meters in length. Further, container 8 can comprise perforation lines 9, 10, 11, and 12, which are illustrated in FIG. 3. Container 8 can be broken along these perforation lines so as to form at least four separate container of various lengths. The dimensions of container 8, including its ability to have a variety of lengths facilitate its positioning at difficult to reach points around the house.

Container 8 can be divided into ten sections each having a length of ten centimeters by perforation lines. Each section, in turn, can be divided into two 5-centimeter sections by perforation lines.

In addition, container 8 also comprises retention sections 17 and 18 extending inwardly and downwardly from the top of substantially vertical walls 1 and 2 for retaining the insecticide inside container 8. Finally, the lateral walls of container 8 that comprise laterally extending surfaces on vertical walls 1 and 2 can be used for advertising purposes.

Although the invention has been described with respect to particular means, methods, and embodiments, and although the invention has been described with respect to particular shapes, dimensions, and arrangements of the various elements, the invention is not limited thereto, but extends to all equivalents within the scope of the claims.

What is claimed is:

1. A container adapted for housing an insecticide comprising:
    (a) a plurality of side walls, each of said side walls comprising an upper portion, each said upper portion comprising a retention section extending inwardly and downwardly from said upper portion;
    (b) a bottom wall connecting said side walls, wherein said container is open at the top thereof, said side walls and said bottom wall forming a continuous canal having a substantially U-shaped transverse cross-section and forming a substantially parallelepipedic volume therein, said retention sections extending towards an inner surface of said bottom wall, said retention sections comprising means for retaining said insecticide within said container irrespective of the position of said container open at top, wherein said bottom wall comprises an exterior surface including a self-adhesive lining,
    wherein said insecticide substantially fills said parallelepipedic volume and comprises a boric acid base, sugar molasses, and starch comprising flour and forms a substantially pasty mixture positioned in said container, wherein said insecticide adheres to said walls of said container and is substantially hygrometrically stable.

2. The container and insecticide combination defined by claim 1 wherein the proportion of boric acid, sugar molasses, and flour by weight is 3:2:1, respectively.

3. The container and insecticide combination defined by claim 1 wherein the proportion of boric acid, sugar molasses and flour by weight is 3:2:2, respectively.

4. The container and insecticide combination defined by claim 1 wherein said insecticide comprises an agent limiting the fluidity of said insecticide.

5. The container and insecticide combination defined by claim 1 wherein said container has a predetermined length, wherein said container further comprises at least one perforation line extending along said side walls substantially perpendicular to said bottom wall, wherein said at least one perforation line comprises means for separating said container along said perforation line into two containers each having a length shorter than said predetermined length of said container.

6. The container and insecticide combination defined by claim 1 wherein said container comprises a plurality of spaced apart perforation lines.

7. The container and insecticide combination defined by claim 1 wherein said self-adhesive lining comprises means for positioning said container on a vertical wall, a ceiling, or the ground.

8. The container and insecticide combination defined by claim 7 further comprising a protective film removably attached to said self-adhesive lining.

* * * * *